United States Patent [19]

Hudkicky et al.

[11] Patent Number: 5,777,137
[45] Date of Patent: Jul. 7, 1998

[54] PANCRATISTATINS AND PROCESSES FOR THEIR PRODUCTION

[75] Inventors: Tomas Hudkicky, Gainesville, Fla.; Kurt Königsberger, Oberndorf, Austria; Sherita D. McLamore, Gainesville, Fla.; Rakesh Maurya, Jammu, India

[73] Assignee: University of Florida, Gainesville, Fla.

[21] Appl. No.: 548,367

[22] Filed: Nov. 1, 1995

[51] Int. Cl.$^6$ .................. C07D 307/00; C07D 317/00; C07D 323/02

[52] U.S. Cl. .................. 549/435; 549/432; 549/434; 549/439

[58] Field of Search .................. 536/18.5, 120; 549/432, 434, 435, 439

[56] References Cited

FOREIGN PATENT DOCUMENTS

WO 95/35303A 12/1995 WIPO.
WO 96/25414A 8/1996 WIPO.

OTHER PUBLICATIONS

Hudlicky et al., "Toluene Dioxygenase–Mediated Cis–Dihydroxylation of Aromatics in Enantiodelective Synthesis. Asymmetric Total Synthesis of Pancratistatin and 7–Deoxypancratistatin, Promising Antitumor Agents". J. Am. Chem. Soc., 118:10752–10765, 1996.

Tian et al., "Asymmetric Total Synthesis of (+)–7–Deoxypancratistatin", Synlett, 1125–1126, Nov., 1995.

Angle, Steven R. and Louie, Michael S., "Quinone Methide Initiated Cyclization Reactions: Studies Toward The Synthesis of (+)–Pancratistatin", Tetrahedron Letters, 34:30(4751–4754, 1993.

Banwell et al., "Lycoricidine and Pancratistatin Analogues from Cyclopentadiene", J. Chem. Soc. Perkin Trans., 3515–3518, 1994.

Danishefsky, Samuel and Lee, Joung Yon, "Total Synthesis of (±)–Pancratistatin", J. Am. Chem. Soc., 111:4829–4837, 1989.

Doyle et al., "A Novel Case of Cationic Rearrangement Involving a Phenonium Ion", Tetrahedron Letters, 35(45):8295–8298, 1994.

Fioravanti et al., "A Facile Aziridination of Allylic and Homoallylic Cyclic Acetals", Tetrahedron Letters 34(27):4353–4354, 1993.

Gabrielsen et al., "antiviral (RNA) Activity of Selected Amaryllidaceae Isoquinoline Constituents and Synthesis of Related Substances", Journal of Natural Products, 55(11):1569–1581, Nov. 1992.

Hudlicky et al., "A Model Study Directed Towards a Practical Enantioselective Total Synthesis of ( –)–Morphine", Synthesis, pp. 174–178, Jan./Feb. 1992.

Keck et al., Abstract #478, Anaheim Book of Abstracts, 209th ACS National Meeting, Apr. 2–6, 1995.

Khaldi et al., "A Short Route to Enantiomerically Pure Narciclasine Derivatives", Tetrahedron Letters, 36(17):3003–3006, 1995.

Lopes et al., "Synthesis of Pancratistatin Models", Tetrahedron Letters, 33(45):6775–6778, 1992.

Martin et al., "Diastereoselective [4+2]Cycloadditions of Acyl Nitroso Compounds", Tetrahedron Letters, 33(25):3583–3586, 1992.

Ohta & Kimoto, "Synthetic Studies on Lycoricidine and Related Compounds", Chem. Pharm. Bull., 24(12):2977–2984, 1976.

Ohta & Kimoto, "Total Synthesis of ( ±)–Lycoricidine", Tetrahedron Letters, 27:2279–2282, 1975.

Park & Danishefsky, "A Concise Route to Enantiomerically Pure 2–Arylcyclohexenones of Relevance to the Pancratistatin Problem", Tetrahedron Letters, 36(2):195–196, 1995.

Paulsen & Stubbe, "Chirale Synthese Von ( +)–Lycoricidin", Tetrahedron Letters, 23(31):3171–3174, 1982.

Paulsen & Stubbe, "Synthese Von Enantionmerenreinem (+)–Lycoricidin Aus D–Glucose", Liebigs Ann. Chem., 535–556, 1983.

Pettit et al., "Antineoplastic Agents, 105. Zephyranthes Grandiflora", Journal of Natural Products, 47(6):1018–1020, Nov.–Dec. 1984.

Pettit et al., "Antineoplastic Agents, 120. Pancratium Littorali", Journal of Natural products, 49(6):995–1002, Nov.–Dec. 1986.

Pettit et al., "Antineoplastic Agents, 162. Zephyranthes Candida", Journal of Natural Products, 53(1):176–178, Jan.–Feb. 1990.

Thompson & Kallmerten, "an Annulative, Carbohydrate–Based Approach to Pancratistatin and Structurally Related Phenanthridone Alkaloids. Synthesis of (+)–Tetrabenzyllycoricidine", Journal of Organic Chemistry, 55:6076–6078, 1990.

Tian et al., "First Enantioselective Total Synthesis of (+)–Pancratistatin: An Unusal Set of Problems", J. Am. Chem. Co., 117:3643–3644, 1995.

Trost & Pulley, "Asymmetric Total Synthesis of (+)–Pancratistatin", J. Am. Chem. Soc., 117:10143–10144, 1995.

Primary Examiner—Elli Peselev
Attorney, Agent, or Firm—Arnold, White & Durkee

[57] ABSTRACT

Disclosed are novel pancratistatins and methods for their total asymmetric synthesis. In particular embodiments, processes for the total asymmetric synthesis of (+)-pancratistatin, (−)-pancratistatin, (+)-7-deoxypancratistatin, (−)-7-deoxypancratistatin, truncated pancratistatins, and related derivatives are provided.

1 Claim, No Drawings

PANCRATISTATINS AND PROCESSES FOR THEIR PRODUCTION

BACKGROUND OF THE INVENTION

The United States government has certain rights in the present invention pursuant to Grant number CHE-9521489 from the National Science Foundation.

A. Field of the invention

This invention relates to methods for the preparation of pancratistatins. In a preferred embodiment, the invention provides novel processes for the total asymmetric synthesis of 7-deoxypancratistatin and related compositions.

B. Description of the related art 1. (+)-Pancratistatin

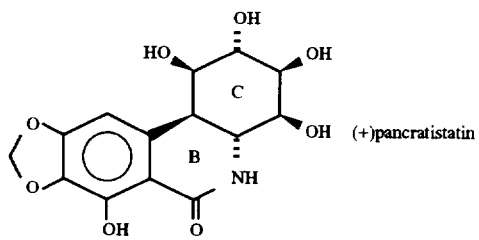

(+)-Pancratistatin, an antimitotic member of the Amaryllidaceae alkaloids has been shown effective against lymphatic leukemia and ovarian cancer (Pettit et al., 1984; Baez et al., 1978). Its antineoplastic activity and ability to inhibit protein synthesis has made it an attractive candidate for exploitation as an anticancer therapeutic. Previously, its only source was isolation of the crude alkaloid from the plant species *Pancratium littorale* (Pettit et al., 1986).

In view of the anti-tumor activity of pancratistatin, there have been numerous attempts to develop an efficient total synthesis. While synthetic procedures have been developed, such syntheses are relatively inefficient and involve a large number of steps. Attempts at the synthesis of (+)-pancratistatin have been made (Thompson and Kallmerten, 1990), but the total synthesis was not achieved due to the failure to elaborate the required transfused phenanthridones. Total synthesis of (±)-pancratistatin, however, has been accomplished in a thirty-step reaction (Danishefsky and Lee, 1989), but this synthesis was plagued by low yields, with the process yielding the racemic mixture.

A recent report by Angle and Louie (1993) has suggested a functionalized cyclohexenone might serve as a precursor for (+)-pancratistatin, but no specific synthesis was proposed. The only other reported attempts at the total synthesis of *Amaryllidaceae* alkaloids such as 7-deoxypancratistatin involve the use of either gluconolactone derivatives and bromoalcohols (Keck et al., 1995) or symmetrical diols prepared from benzoquinone (Trost and Pulley, 1995) as precursors. Recently, amino cyclitols have been proposed as possible intermediates for pancratistatin synthesis (Hudlicky et al., 1994).

2. 7-Dexoypancratistatin

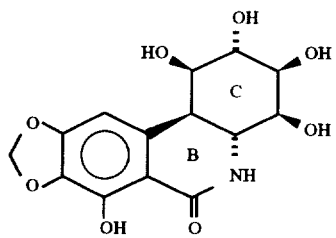

7-dexoypancratistatin was isolated in 1989 from *Haemanthus kalbreyeri* by Ghosal and coworkers (1989) and has been shown to have a promising therapeutic index in in vitro antitumor screening (Gabrielsen et al., 1992). Synthetic ventures aimed at its efficient preparation (Paulsen and Stubbe, 1983; Keck et al., 1995) and preparation of its congeners, pancratistatin (Danishefsky and Lee, 1989; Tian et al., 1995), lycoricidine (Chida et al., 1991Paulsen and Stubbe, 1983; Paulsen and Stubbe, 1982; Ohta and Kimoto, 1976; Ohta and Kimoto, 1975; Chida et al., 1993; Johnson and Su, 1993; Martin and Tso, 1993), and narciclasine (Khaldi et al., 1995) abound in the chemical literature, with the most recent synthesis reported by Keck (1995).

3. Deficiencies in the Prior Art

Unfortunately, despite ongoing efforts to develop an efficient asymmetric chemical synthesis of pancratistatin and related compounds, progress has been slow. Isolation from plant sources is currently limited and expensive, thus severely limiting development of pancratistatin as a therapeutic agent. Moreover, as with many biologically active compounds isolated from natural sources, optimization of activities and minimization of undesirable side effects is frequently achieved by chemical modification of the naturally occurring compound. There is therefore a need for an efficient synthesis of pancratistatin, and specific enantiomers thereof, its precursors, and derivatives to allow development of therapeutically important pancratistatin compounds.

SUMMARY OF THE INVENTION

The present invention overcomes one or more of these and other drawbacks inherent in the prior art by providing novel compositions and processes for the synthesis of pancratistatins. In one embodiment, the invention provides methods for the total asymmetric synthesis of 7-deoxypancratistatin and related compositions. The invention also provides novel precursors and intermediates in the synthesis of these compounds.

In another preferred embodiment, the invention discloses novel processes for the total asymmetric syntheses of (−)-pancratistatin, (+)-pancratistatin, and various truncated intermediates and their derivatives. These processes are described in the examples contained herein, and are illustrated in Scheme 1 and Scheme 2:

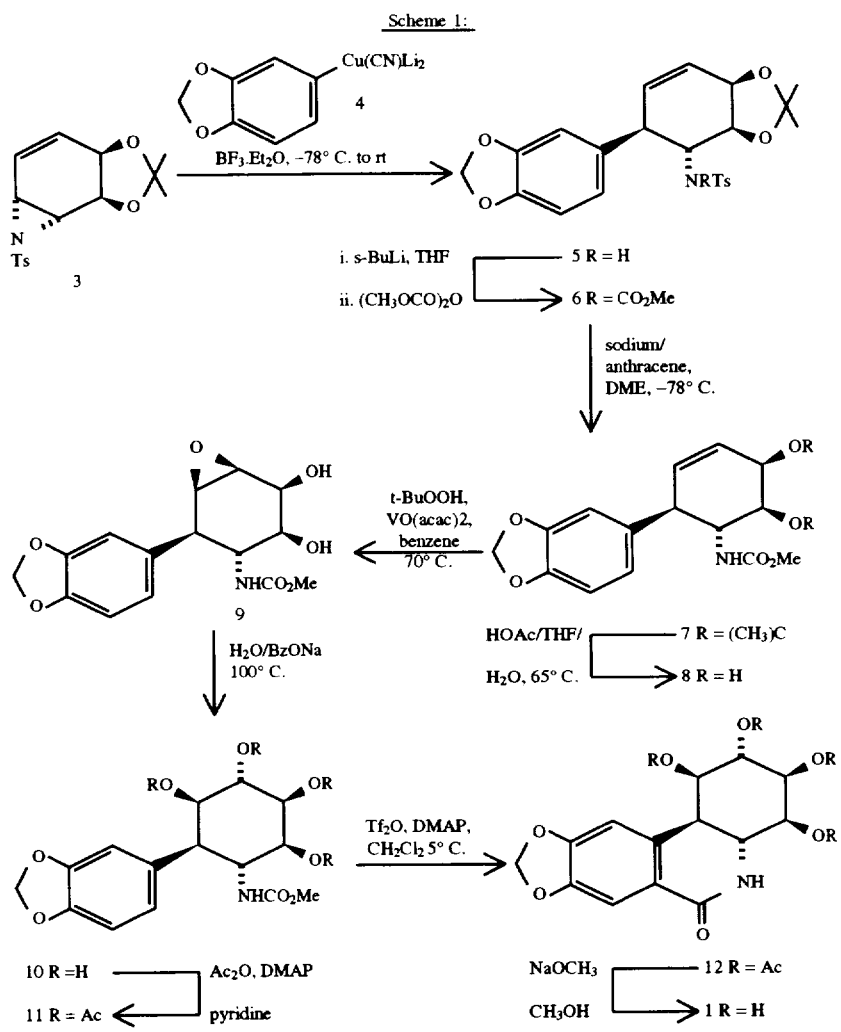
Scheme 1:
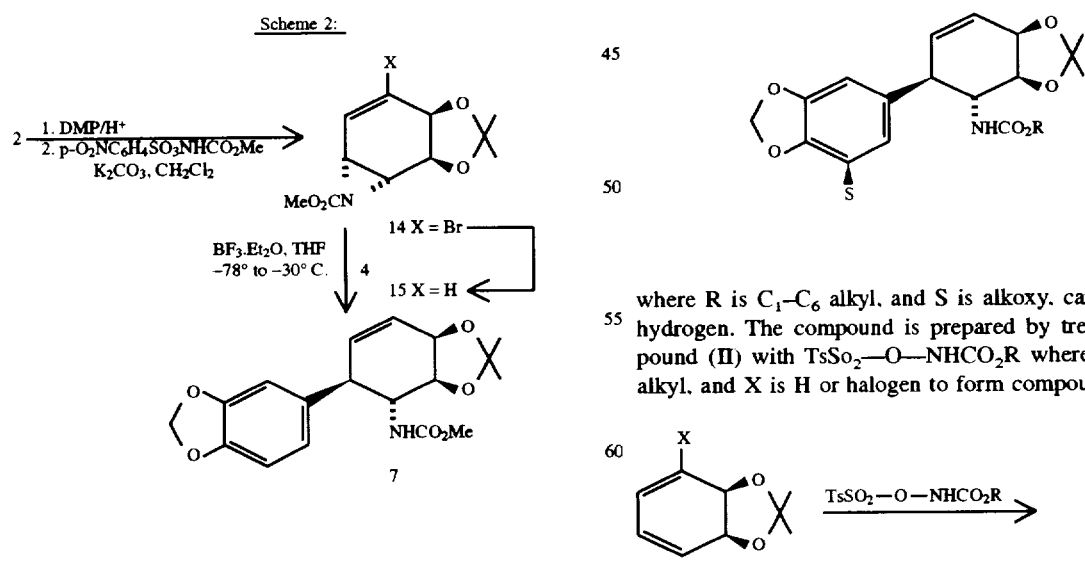
Scheme 2:
where R is $C_1-C_6$ alkyl, and S is alkoxy, carboalkoxy, or hydrogen. The compound is prepared by treating a compound (II) with $TsSO_2$—O—$NHCO_2R$ where R is $C_1-C_6$ alkyl, and X is H or halogen to form compound III:
In a preferred embodiment, the present invention provides a process for the preparation of a (+)-pancratistatin intermediate (I) having the formula:

-continued

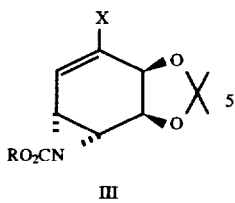

III

Alternatively, III may be prepared by detosylation of the following compound followed by treatment with ClCO₂R.

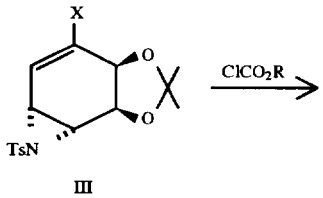

III

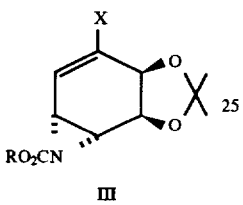

III where R is $C_1$ to $C_6$ alkyl. Compound III is then condensed with a cuprate selected from a group consisting of compounds IV, V and VI:

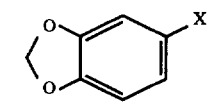

IV

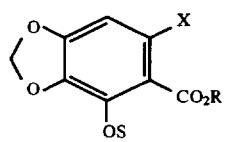

V

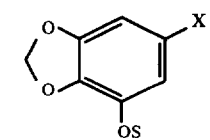

VI where X is a cuprate or a mixed cuprate, selected from the group consisting of CuI, $Cu(CN)Li_2$, and mixed cuprates, and S is a protecting group selected from the group consisting of $CH_3$, $CH_2Ph$, TBS, and TBS to form the pancratistatin intermediate (I).

Other aspects of the invention are the novel carbomethoxyaziridines having the formulas of VII, VIII and IX:

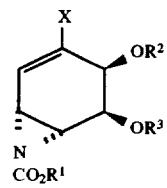

VII

-continued

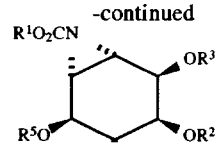

VIII

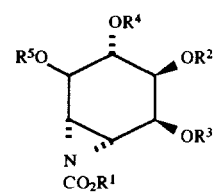

IX where X is hydrogen, Br or Cl; $R^1$ is $C_1$–$C_6$ alkyl; and $R^2$, $R^3$, $R^4$, and $R^5$ are independently hydrogen, $C_1$–$C_6$ branched or straight chain alkyl, alkenyl, alkoxy, acyl, or acetonide.

In a related aspect, the inventors contemplate preparation of compounds X, XI and XII shown below:

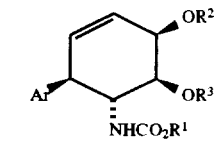

X

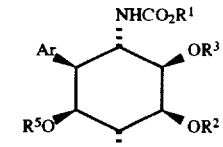

XI

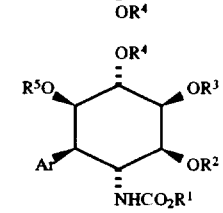

XII where X is H, Cl or Br; $R^1$ is $C_1$–$C_6$ alkyl; $R^2$, $R^3$, $R^4$, and $R^5$ are independently hydrogen, $C_1$–$C_6$ branched or straight chain alkyl, alkenyl, alkoxy or acyl; and Ar is selected from the group consisting of compounds XIII, XIV and XV:

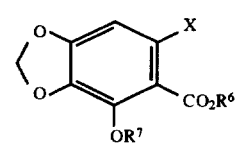

XIII

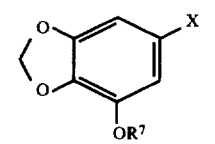

XIV

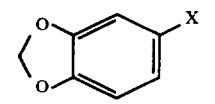

XV where $R^6$ and $R^7$ are independently hydrogen or $C_1$–$C_6$ alkyl, and X is H, Br, or I. These compounds may be obtained by ring opening of the corresponding aziridines shown above.

Yet another aspect of the invention are the novel (XVI) compounds having the formula:

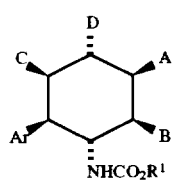

where A, B, C and D are independently D, H, F, Cl, Br, I, OH, or $SR^1$, $OR^1$, $NR^1R^2$ or $SO_2Y$ where $R^1$ and $R^2$ are independently H or $C_1-C_6$ alkyl or alkenyl and Y is halogen, $C_1-C_6$ alkyl, allyl or phenyl except that $SO_2Y$ is not $SO_2H$; and Ar is selected from the group consisting of alkyl, alkoxy, substituted benzenes, heteroaromatics, or compounds such as one of the following:

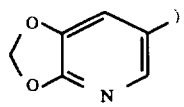

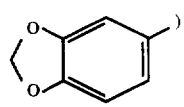

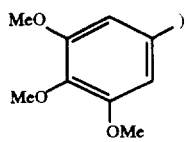

These compounds provide a route to preparation of novel pancratistatin-related compounds and derivatives. Such derivatives may include monosaccharides such as glucose, fructose, inositols, aminocyclitols, sphingosine, and amino acids substituted at the various positions.

Further embodiments of the present invention comprise processes for the preparation of compounds having the generic formula of (XVII) or (XXXII), or of truncated derivatives thereof:

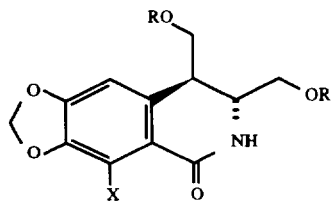

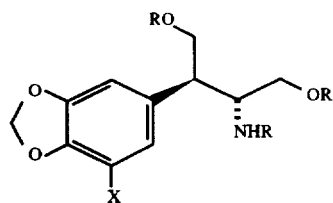

where X is H, R, or OR; R is H, $C_1-C_6$ alkyl, alkoxy or alkenyl. For example, XVII may be prepared by cleaving ring C of the following compound (XVIII), preferably by ozonization, or periodate cleavage.

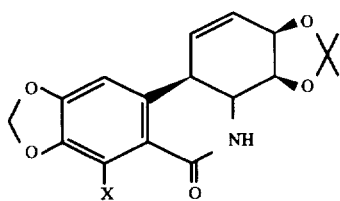

then reducing the product and acidifying to form the following compound (XIX):

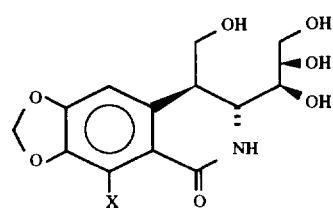

and finally treating the resulting compound with $IO_4^{31}$ and then $NaBH_4$ to form the truncated pancratistatin intermediate.

Another aspect of the invention comprises a process for the preparation of (+)-7-deoxypancratistatin. This process includes first reacting (1R,2R,3S,4S)-1-carbomethoxy-3,4-isopropylidenedioxy-1-azabicyclo[4.1.0] heptene with a cuprate having the following formula (XX), where X is H, R, or OR, and R is as before:

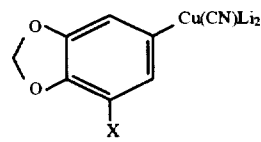

to form a compound having the following formula (XXI):

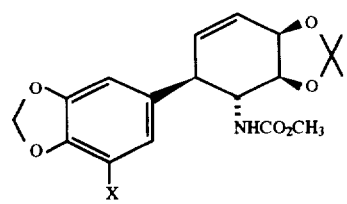

then removing the gem hydroxyl protecting group under suitable acid conditions, and oxidizing the cyclohexenyl ring double bond to form the following epoxide (XXII):

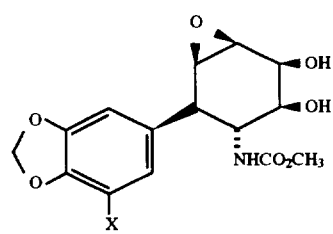

The epoxide ring in stereoselectively opened to form the aryl aminocyclitol (XXIII):

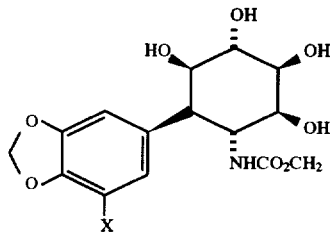

which is then peracetylated to form the following compound (XXIV):

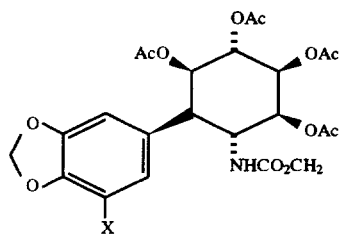

Compound XXIV is cyclized to form compound XXV:

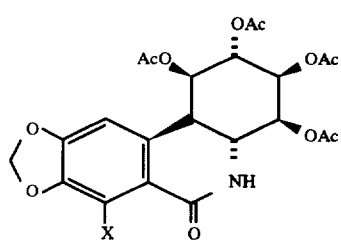

(+)-7-deoxypancratistatin is then obtained by deacetylating compound XXV when X is H. In a preferred embodiment, the cyclization is a modified Bischler-Napieralski cyclization in the presence of Tf$_2$O/DMAP, and the condensation with a cuprate occurs in the presence of boron trifluoride etherate in a suitable solvent, such as tetrahydrofuran, or any higher ether. The gem hydroxyl protecting group may be removed under acidic conditions employing such acids as TfOH, BF$_3$, or other Lewis acids. Oxidation of the cyclohexenyl double bond is preferably accomplished in the presence of O$_3$ in CH$_2$Cl$_2$ or MeOH.

The epoxide ring may be opened under aqueous conditions using sodium aryloxide or alternatively, alcohols in the presence of acid. Peracetylation is typically accomplished with acetic anhydride, although the inventors contemplate than other such compounds may be suitable such as higher alkanoic acid anhydrides. Deacetylation is then accomplished by reducing the acyl groups with sodium methoxide in suitable organic solvents such as methanol or lower alcohols, to obtain (+)-7-deoxypancratistatin.

By employing aziridines having the formula of compounds XXVI and XXVII an efficient route to (+)-pancratistatins and related compounds is now available.

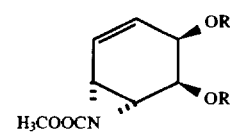

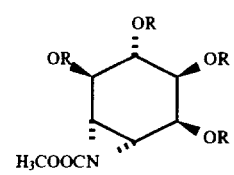

The following aziridine (XXVIII) provides an efficient route to the enantiomer.

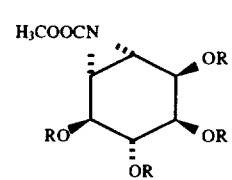

Other aspects of the invention contemplated by the inventors is the possibility for intramolecular variants of the aziridine opening. These methods may be applied to both enantiomeric series:

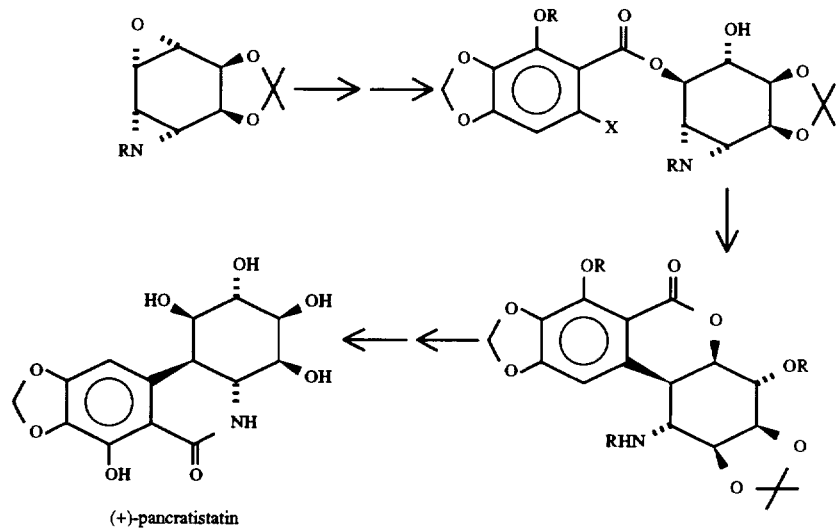

(+)-pancratistatin

-continued

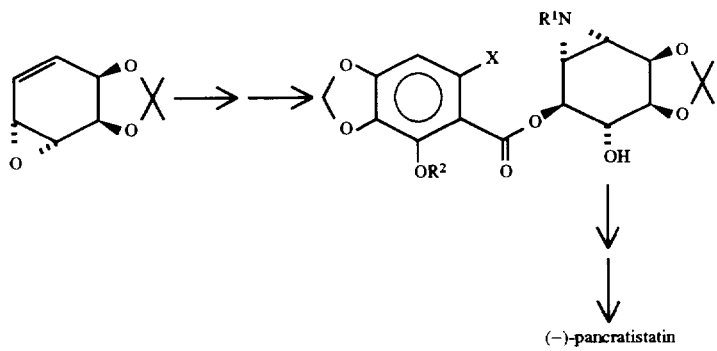

(−)-pancratistatin where X is Li, H or Br; $R^1$ is tosyl, carbomethoxy or H; and $R^2$ is $C_1$–$C_6$ alkyl, alkoxy, alkylene, or allyl. When X is H, a modified Bischler-Napieralski synthesis may be used, and when X is Br, nBuLi metallation conditions may be employed followed by either CuI treatment, or $BF_3$ activation of the aziridine.

Unnatural residues composed of F, Br, Cl, I, OH, or $SR^1$, $OR^1$, $NR^1R^2$ or $SO_2Y$ where $R^1$ and $R^2$ are independently H or $C_1$–$C_6$ alkyl or alkenyl and Y is halogen, $C_1$–$C_6$ alkyl, allyl or phenyl except that $SO_2Y$ is not $SO_2H$, glycosyls, inositols, sphingosines, and any other nucleophilic group may be attached to ring C to systematically probe activity sites and requirements. All such compounds can be made from (XXVII) and (XXVIII) using well-known chemical methods. In addition, isotopically-labeled drugs may be prepared from diols (XXIX) and (XXX). Methods of attachment of inositol and glycosyl and other nucleophilic residues are well-known to those of skill in the art.

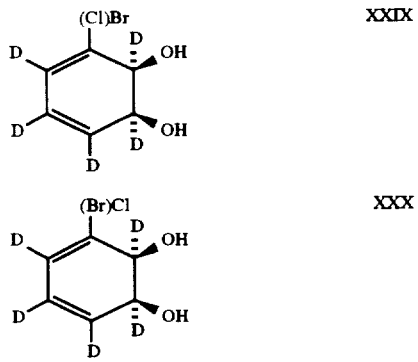

An important aspect of the present invention is the synthesis of carboalkoxy, vinylaziridines that provide novel intermediates for the synthesis of pancratistatin and derivatives of pancratistatin. In contrast to other activated aziridines such as tosyl- or N-carbobenzyloxy-substituted derivatives, N-carboalkoxy compounds overcome several of the problems encountered in the use of previously employed N-substituted aziridines. There is no need to remove the tosyl group, and the amide carbon is provided, therefore the use of groups such as $CONR_2$, which are hard to remove is obviated.

In related aspects of the invention, it now becomes possible to efficiently synthesize several substituted intermediates for pancratistatin synthesis. These include halogenated derivatives of compound X, particularly the chlorine and bromine derivatives, alkyl, alkoxy, alkylene and divalent hydrocarbon radicals, mixed ether groups in compounds X,Y and Z, including $C_1$–$C_6$ alkyl, alkoxy, alkylene and allyl both branched and unbranched chains. Other readily prepared substitutions at these positions include various alkyl and aryl esters, e.g., acetates and benzoates. Other mixed ethers are also contemplated selected from a wide range of compounds, including sugars, such as monosaccharides, cyclitols, amino acids, fatty acids, sphingosines and the like. Methods to attach such groups to the cyclohexane and cyclohexene rings of compounds X, Y and Z are well known to those skilled in the art.

The alkyl of the N-carboalkoxy group is preferably methyl, although other alkyls such as ethyl, methyl, propyl or any one of $C_1$–$C_5$ alkyls branched or unbranched are contemplated.

DETAILED DESCRIPTION OF THE PREFERRED EMBODIMENTS

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Asymmetric Synthesis of Pancratistatins from Tosylaziridine

The following example illustrates the total asymmetric synthesis of 7-deoxypancratistatin 1 starting from 6-bromo-3,5-cyclohexadiene-1,2-diol via Scheme 1. The key step involved is the regioselective ring opening of tosylaziridine 3 with a higher-order cuprate which is followed several steps later by cyclization of urethane 11.

The synthesis sets out from the enantiopure diol 2 (Eastman Fine Chemical, Rochester, NY) prepared from bromobenzene by toluene dioxygenase-mediated whole cell fermentation as previously disclosed (Hudlicky et al., 1992; Gibson et al., 1970). Its conversion to tosylaziridine 3 in three steps was recently reported (Tian et al., 1995). Addition of higher-order cuprate 4 derived from 6-bromo-1,3-benozodioxol provided the crucial trans-substituted tosylamide 5 ($BF_3.Et_2O$, -78° C. to rt, 32%). Acylation with dimethyl pyrocarbonate gave the urethane 6 (76%) which was reduced to 7 (73%), Scheme 1.

Deprotection to the free diol 8 (98%) followed by epoxidation to 9 (50%) and stereoselective ring opening of the epoxide with water in the presence of a catalytic amount of sodium benzoate provided the aryl aminocyclitol 10 in 82% yield. After peracetylation, furnishing the cyclization precursor 11 (84%), the conditions reported by Banwell for the Bischler-Napieralski type cyclization (1994) were utilized. Exposure of 11 to Tf$_2$O/DMAP gave tetraacetate 12 (61%), which was isolated and proved identical to the compound prepared by Keck ([α]$_D$/NMR/TLC). Treatment of 12 with NaOCH$_3$ smoothly generated 1 in 72% yield, whose properties matched those reported in the literature (Paulsen and Stubbe, 1983). [NMR, [α]$_D^{25}$=+78.5° (c0.75,DMF); lit. (Paulsen and Stubbe, 1983) [α]$_D^{20}$=+82.6° (c 1.1, DMF)].

The synthesis of 1 was thus accomplished in nine steps from aziridine 3 in an overall yield of 2.6%. This approach solved adequately the problem of benzamide manipulation encountered during earlier synthesis of pancratistatin (Tian et al., 1995).

EXAMPLE 2

Novel Asymmetric Synthesis of Pancratistatins from a Novel Carbomethoxyaziridine Intermediate The following example illustrates the total asymmetric synthesis of 7-deoxypancratistatin 1 starting from 6-bromo-3,5-cyclohexadiene-1,2-diol via Scheme 2 using a novel carbomethoxyaziridine for an overall yield of 3.0%. Following reduction to yield 7,the synthesis proceeds as in Scheme 1. To circumvent the problems associated with the manipulations of benzamide, which plagued earlier efforts toward pancratistatin (Tian et al., 1995), this scheme cyclized the amide in 1 in the last step of the synthesis.

A. Selected Experimental Procedures 1. (3R,4R,5S,6R)-5,6-Isopropylidenedioxy-3-[3,4-methylenedioxy)-phenyl\-4-)4-methylphenylsulfonylamino)-1-cyclohexene (5)

n-BuLi (1.94 M in hexane, 10 mL) was added to a solution of 6-bromo-1,3-benzodioxol (16.6 mmol) in THF (65 mL) at −78° C. The reaction mixture was stirred for 40 min at −78° C. and CuCN (744 mg, 8.3 mmol) was added. After stirring at −78° C. for 1 h, a solution of aziridine 3 (1.27g, 3.95 mmol) in THF (10 mL) was added, followed by BF$_3$.Et$_2$O (0.40 mL). The reaction mixture was allowed to warm slowly to room temperature while stirring. After addition of saturated aqueous NH$_4$Cl solution (10 mL), the organic layer was separated and the aqueous phase was extracted with ethyl acetate (4×10 mL). The combined organic layers were dried over Na$_2$SO$_4$ and concentrated under reduced pressure. The residue was purified by column chromatography (silica gel, CH$_2$Cl$_2$/acetone, 12:1) to give tosylamide 5 (552 mg, 32%) as a white solid: mp 75°-76° C.; [α]$_D^{22}$+44.6° (c 1.16, CHCl$_3$); $^1$H NMR (200 NMz, CHCl$_3$) δ 7.43 (d, J=8.2 Hz, 2H), 7.09 (d, J=8.2 Hz, 2H), 6.49 (m, 3H), 5.95 (m,3H), 5.76 (dd, J=9.9, 1.6 Hz, 1H), 5.34 (d, J=8.5 Hz, 1H), 4.61 (t, J=4.46 Hz, 1H), 4.13 (dd, j=9.1, 6.0 Hz, 1H), 3.51 (q, J=9.2 Hz, 1H), 3.13 (bd, J=9.8 Hz, 1H), 2.38 (s, 3H), 1.50 (s, 3H), 1.35 (s, 3H); $^{13}$C NMR (50 MHz, C$_6$D$_6$) δ 147.9 (C), 146.9 (C), 141.6 (C), 140.6 (C), 135.1 (CH), 135.0 (C), 129.0 (CH), 126.9 (CH), 124.3 (CH), 122.3 (CH), 109.9 (C), 109.2 (CH), 108.4 (CH), 100.7 (CH$_2$), 78.2 (CH), 72.7 (CH), 59.6 (CH) 47.5 (CH), 28.3 (CH$_3$), 26.3 (CH$_3$), 21.1 (CH$_3$); HRMS: calculated for C$_{23}$H$_{25}$O$_6$NS 443.1403, found 443.1416.

2. (1R,2R,3S,4S)-1-Carbomethoxy-3,4-isopropylidenedioxy-1-azabicyclo[4.1.0] heptene Potassium carbonate (1.79 g, 13.0 mmol) was added to a solution of methyl p-nitrophenylsulfonyloxycarbamate (3.59 g, 13.0 mmol) and diene 2 (0.50 g, 2.16 mmol) in dichloromethane (20 mL) and stirred vigorously for 4 hours at room temperature. After filtration and concentration in vacuo, chromatographic purification (silica gel, hexane/EtO Ac, 80:20) afforded 530 mg (80.5%) of colorless oil: $^1$H NMR (300 MHz, CDCL$_3$) δ 6.48 (dd, J=1.4, 5.0 Hz, 1H), 4.90 (ddd, J=6.1, 1.9, 0.8 Hz, 1H), 4.48 (dd,J=6.3, 1.4 Hz, 1H), 3.75 (s, 3H), 3.20 (dd, J=5.8, 1.6 Hz, 1H), 2.98 (t,J=4.9 Hz, 1H), 1.45 (s, 3H), 1.42 (s, 3h);$^{13}$ C NMR (75 MHz, CDCL3) δ161.9, 128.3, 125.7, 111.2, 73.8, 72.2, 53.9, 35.3, 34.9, 27.5, 26.1; HRMS calculated for C$_{11}$H$_{15}$BrO$_4$ 304.0184, found 304.0185; Anal. calculated for C$_{11}$H$_{15}$NBrO$_4$ C 43.44%, H 4.63%, N 4.60%, found C 43.64%, H 4.73%, N 4.55%.

B. Results

This example describes a novel abbreviated synthesis of 1 that may be amenable to a large scale preparation of this alkaloid as well as its congeners. A problem of the previous syntheses, (i.e., manipulation of the tosyl group of its replacement with the carbamate necessary for the cyclizarion) was overcome with this new process (Scheme 2) which also provided novel intermediates useful in the syntheses of related alkaloids.

To reduce the number of functional group interconversions the new aziridine 14 was prepared, as shown in Scheme 2, by adaption of a procedure used for the carboethoxyaziridination of simple olefins (Lwowski and Maricich, 1965; Fioravanti et al., 1993). Thus, after protection of 2 as the acetonide (2,2-dimethoxypropane, p-TSA) aziridine 14 was obtained in 80% yield with methyl p-nitrophenylsulfonyloxycarbamate (Lwowski et al., 1963; Leuenberger et al., 1982)/K$_2$CO$_3$ and reduced to 15 with Bu$_3$SnH/AIBN in 54% yield. Addition of the organocuprate 4 in the presence of BF$_3$.Et$_2$O gave 7 in 34% yield and four steps from 2 overall.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text:

Angle and Louie, Tetrahedron Lett., 34:4751, 1993.
Baez et al., Biochim. Biophys. Acta. 518:95, 1978.
Banwell et al., Chem. Soc., Perkin Trans., 1:3515, 1994.
Chida et al., J. Org. Chem., 58:4441, 1993.
Chida et al., Tetrahedron Lett., 32:4525, 1991.
Clark and Souchet, Tetrahedron Lett., 31:193, 1990.
Danishefsky and Lee, J. Am. Chem. Soc., 1114829, 1989.
Doyce et al., Tetrahedron Lett., 35:8295, 1994.
Fioravanti et al., Tetrahedron Lett., 34:4353, 1993.

Gabrielsen et al., *J. Nat. Prod.*, 55:1569, 1992.
Ghosal et al., *Phytochemistry*, 1693, 1989.
Gibson et al., *Biochemistry*, 9:1626, 1970.
Hudlicky et al., *Synthesis*, 174, 1992. Johnson and Su, "Synthesis of (+)-and (−)-lycoricidine via lipase resolution of conduramines," Abstr. Nat. Organ. Symp., Bozeman, MT, 1993. Keck et al., "A Radical Cyclization Approach to 7-deoxypancratistatin and Related *Amaryllidaceae alkaloids*," Abstr. Ann. Meet. Am. Chem. Soc., Abst. 209(1–2); Abst. #478, Anaheim, Calif., 1995.
Khaldi et al., *Tetrahedron Lett.*, 36:3003, 1995.
Leuenberger et al., *Helv. Chim. Acta*, 65:217, 1982.
Lopes et al., *Tetrahedron Lett.*, 33:6775, 1992.
Lwowski and Maricich, *J. Am. Chem. Soc.*, 87:3630, 1965.
Lwowski et al., 85:1200, 1963.
Martin and Tso, *Abstr. Nat. Organ. Symp.*, Bozeman, MT, 1993. 35:85, 1993.
Martin, et al., *Tetrahedron Lett.* 33(25):3583-3586, 1992.
Ohta and Kimoto, *Chem. Pharm. Bull.*, 24:2977, 1976.
Ohta and Kimoto, *Tetrahedron Lett.*, 2279, 1975.
Park and Danishefsky, *Tetrahedron Lett.*, 36:195, 1995.
Paulsen and Stubbe, *Liebigs Ann, Chem.*, 535, 1983.
Paulsen and Stubbe, *Tetrahedron Lett.*, 23:3171, 1982.
Pettit et al., *J. Nat. Prod.* 49:995, 1986.
Pettit et al., *J. Nat. Prod.* 53:176, 1990.
Pettit et al., *J. Nat. Prod.* 47:1018 1984.
Thompson and Kallmerten, *J. Org. Chem.*, 55:6076, 1990.
Tian et al., *J. Am. Cehm. Soc.*, 117:3643, 1995.
Trost and Pulley, *J. Am. Chem. Soc.*, 117:10143, 1995.

What is claimed is:

1. A process for the preparation of a compound having the formula

I where $R_1$ is $C_1$–$C_6$ alkyl, S is alkoxy or carboalkoxy or hydrogen, comprising the steps of:

a) treating a compound having the formula II with $TsSO_2ONHCO_2R^2$;

II where X is hydrogen or halogen and $R^2$ is $C_1$–$C_6$ allyl, to form III;

III where $R^2$ is as before; and b) condensing compound III with a cuprate selected from a a group consisting of compound IV, V, and VI:

IV

V

VI where $R^1$ is as before, P is a protecting group, and X is a cuprate, selected from the group consisting of CuI, CuCN, and mixed cuprates, to form compound I.

* * * * *

UNITED STATES PATENT AND TRADEMARK OFFICE
CERTIFICATE OF CORRECTION

PATENT NO.    :   5,777,137

DATED         :   July 7, 1998

INVENTOR(S)   :   Tomas Hudlicky, Kurt Königsberger, Sherita McLamore and Rakesh Maurya It is certified that error appears in the above-identified patent and that said Letters Patent is hereby corrected as shown below:

On the cover page, at [75], please delete [Hudkicky] and substitute therefor --Hudlicky--.

Col. 16, line 21, please delete [a].

Signed and Sealed this

Twentieth Day of October, 1998

Attest:

BRUCE LEHMAN

*Attesting Officer*    *Commissioner of Patents and Trademarks*